(12) United States Patent
Schmuck

(10) Patent No.: US 10,271,838 B2
(45) Date of Patent: Apr. 30, 2019

(54) LAPAROSCOPIC SUTURING GUIDE

(71) Applicant: Artisan Medical Supply Corporation, Medford, NJ (US)

(72) Inventor: Michael Schmuck, Pottstown, PA (US)

(73) Assignee: Artisan Medical Supply Corporation, Medford, NJ (US)

( * ) Notice: Subject to any disclaimer, the term of this patent is extended or adjusted under 35 U.S.C. 154(b) by 435 days.

(21) Appl. No.: 14/804,682

(22) Filed: Jul. 21, 2015

(65) Prior Publication Data

US 2017/0020515 A1   Jan. 26, 2017

(51) Int. Cl.
 *A61B 17/04* (2006.01)
 *A61B 17/00* (2006.01)

(52) U.S. Cl.
 CPC ...... *A61B 17/0482* (2013.01); *A61B 17/0057* (2013.01); *A61B 17/00234* (2013.01); *A61B 2017/00637* (2013.01); *A61B 2017/00663* (2013.01)

(58) Field of Classification Search
 CPC .......... A61B 17/0482; A61B 17/00234; A61B 17/0057; A61B 2017/00637; A61B 2017/00663
 USPC ...................................................... 606/148
 See application file for complete search history.

(56) References Cited

U.S. PATENT DOCUMENTS

| 4,337,770 A * | 7/1982 | Young | A61M 39/225 604/30 |
|---|---|---|---|
| 5,417,699 A * | 5/1995 | Klein | A61B 17/0057 112/169 |
| 5,507,758 A * | 4/1996 | Thomason | A61B 17/0469 606/139 |
| 5,830,232 A | 11/1998 | Hasson | |
| 8,465,476 B2 * | 6/2013 | Rogers | A61B 1/00149 128/898 |
| 8,545,522 B2 | 10/2013 | Shpaichler et al. | |
| 2006/0030868 A1 | 2/2006 | Bennett, III | |
| 2011/0178399 A1* | 7/2011 | Del Corso | A61B 17/00491 600/431 |
| 2012/0035623 A1* | 2/2012 | Bagaoisan | A61B 17/0482 606/144 |
| 2013/0103057 A1 | 4/2013 | Keating et al. | |
| 2016/0278763 A1* | 9/2016 | Beaven | A61B 17/0469 |

FOREIGN PATENT DOCUMENTS

WO   WO20141169215 A2 *   4/2013   ......... A61B 17/0057

* cited by examiner

*Primary Examiner* — Shaun David
(74) *Attorney, Agent, or Firm* — Norman E. Lehrer

(57) ABSTRACT

A device for accurately guiding and positioning a surgical instrument bearing suture material to a predetermined area within the body for closing an open wound includes an elongated conically shaped guide that is wider at the top and which has two openings in the side wall thereof. The top has two openings that communicate with the openings in the side wall through generally linear passageways that pass through the guide and which allow surgical instruments carrying suture material to pass therethrough. A thin elongated rod extends upwardly from the top wall approximately two inches and includes a handle at the top thereof. Raising the handle above the guide increases the field of view of the surgeon.

10 Claims, 1 Drawing Sheet

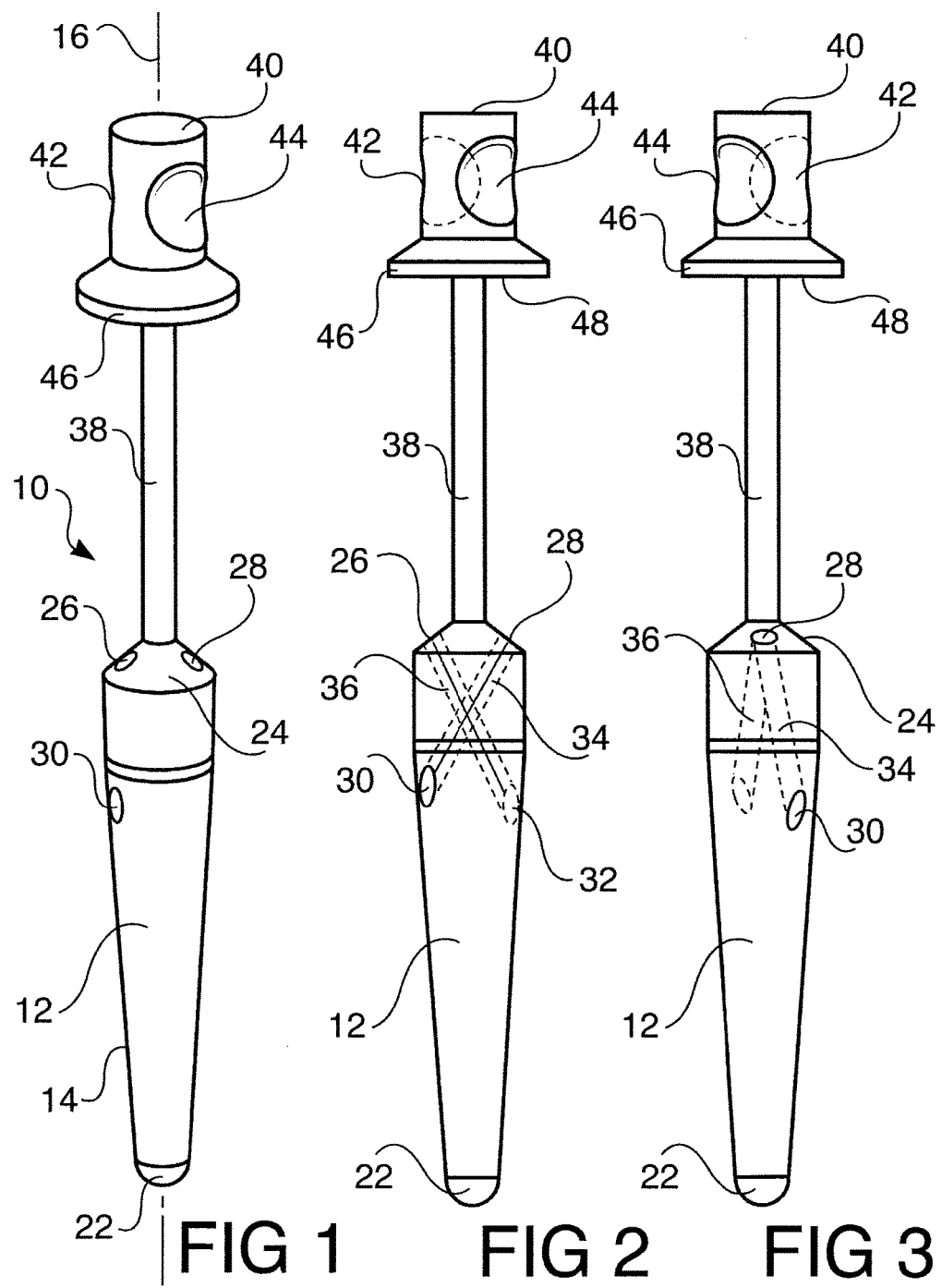

LAPAROSCOPIC SUTURING GUIDE

BACKGROUND OF THE INVENTION

The present invention is directed toward a laparoscopic suturing guide and more particularly, toward such a laparoscopic suturing guide that allows a surgeon to quickly and accurately suture a port after laparoscopic or endoscopic surgery and without inadvertently also suturing the dermis.

As is well known in the art, an endoscopic or laparoscopy procedure involves making small surgical incisions in a patient's body for the insertion of trocar tubes thereby creating access ports into the patient's body. Various types of endoscopic or laparoscopic instruments are passed through these access ports and the appropriate surgical procedures are carried out.

After the surgical procedure is performed, the trocar tubes are removed and the incisions sutured closed by using a needle and grasper for penetrating the tissue and handling the suture. This procedure for closure is frequently time-consuming requiring the identification of the fascia and closure of each fascial site with suture from an external point.

The necessity for properly closing these port sites, particularly in laparoscopic surgery, is critical since suturing the incisions improperly can lead to bowel herniation through the port sites as well as the possibility of omental trapping if the fascial sites are not properly closed. Incisional hernias have occurred in both laparoscopic-assisted vaginal hysterectomies and laparoscopic cholecystectomies as well as other advanced laparoscopic procedures.

At present, two methods of wound suturing upon the removal of the ports are known. According to one of them, the wound is sutured manually with the help of surgical thread-guiding members such as clamp needles and without any special devices. This method is highly traumatizing and labor-consuming as the selection of the right directions of the thread-guiding members inserted through the abdominal or thoracic wall into the pre-specified points of the body requires quite a considerable amount of time.

The other method involves the use of special devices or guides which diminish the traumatizing effect of wound suturing and the amount of labor required. One such device is described, for example, in U.S. Pat. No. 5,507,758 that issued to Thomason et al. in 1996.

The Thomason et al. guide comprises a cylindrical main section which at its proximal end comprises a disk-like projection. The cylindrical section of the guide is inserted into the port until the peripheral projection at the proximal end bears as an abutment on the outer side of the tissue, i.e. on the surface of the skin. Two obliquely running through-holes are formed in the inside of the cylindrical section, so that instruments for suturing may be introduced from the proximal end-face of the guide into the through-holes. The through-holes are opened to the peripheral outer wall of the cylindrical section, such that instruments used for suturing enter the tissue through an exit hole and penetrate this tissue in order to suture.

While the Thomason et al. device has met with some success, it is not completely satisfactory. When closing the port, it is necessary to initially suture only the abdominal or the thoracic wall or the peritoneum facia and to avoid the suturing needle from passing through the epidermis or the dermis or other layer of skin. This is sometimes difficult to do with the use of the Thomason et al. device since the disk-like projection at the top or proximal end covers the site and prevents the surgeon from properly viewing the same. As a result, the surgeon closing the port cannot see precisely where the suture needle is entering the port and it sometimes occurs that the needle enters too high and passes through the dermis.

A need exists, therefore, for a laparoscopic suturing guide that allows a surgeon to quickly and accurately suture a port after laparoscopic or endoscopic surgery.

SUMMARY OF THE INVENTION

The present invention is designed to overcome the deficiencies of the prior art discussed above. It is an object of the present invention to provide a laparoscopic suturing guide that allows a surgeon to quickly and accurately suture a port after laparoscopic or endoscopic surgery.

It is another object of the present invention to provide a laparoscopic suturing guide that allows a surgeon to quickly and accurately suture a port after laparoscopic or endoscopic surgery and which is designed to provide an open field of view for the surgeon.

It is a still further object of the present invention to provide such a laparoscopic suturing guide that allows a surgeon to quickly and accurately suture a port after laparoscopic or endoscopic surgery and without inadvertently also suturing the dermis.

In accordance with the illustrative embodiments demonstrating features and advantages of the present invention, there is provided a laparoscopic suturing guide device for accurately guiding and positioning a surgical instrument bearing suture material to a predetermined area within the body for closing an open wound. The device includes an elongated conically shaped guide that is wider at the top and which has two openings in the side wall thereof. The top has two openings that communicate with the openings in the side wall through generally linear passageways that pass through the guide and which allow surgical instruments carrying suture material to pass therethrough. A thin elongated rod extends upwardly from the top wall approximately two inches and includes a handle at the top thereof. Raising the handle above the guide increases the field of view of the surgeon.

Other objects, features, and advantages of the invention will be readily apparent from the following detailed description of the preferred embodiment thereof taken in conjunction with the drawings.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 1 is a top front perspective view of the laparoscopic suturing guide of my invention;

FIG. 2 is a front elevational view thereof, and

FIG. 3 is a side elevational view thereof.

DETAILED DESCRIPTION OF THE PREFERRED EMBODIMENTS

Referring now to the drawings in detail wherein like reference numerals have been used throughout the various figures to designate like elements, there is shown in FIGS. 1-3 a laparoscopic suturing guide device constructed in accordance with the principles of the present invention and designated generally as 10.

The laparoscopic suturing guide device 10 is comprised of a guide means 12 having a substantially elongated conical shape with an outer conical wall 14. The guide means is approximately 3 inches long although it may vary depending on the specific laparoscopic procedure. In any event, the guide means includes a longitudinal axis 16 and is somewhat smaller at the lower distal end 18 than at the upper proximal end 20. In the preferred embodiment, the guide means 12 tapers from about ⅝ inches at the proximal end 20 to about ¼ inch adjacent the distal end 18.

The lower distal end 18 has a rounded end 22 and is adapted to be inserted into the laparoscopic incision or wound as is, per se, well known in the art. The upper proximal end 20 of the guide means 12 includes an upper was 24 which is preferably substantially convex in that it is higher at its center than at its side edge. First and second spaced apart openings 26 and 28 are formed in the convex wall 24 approximately 180 degrees apart from each other. These openings communicate with openings 30 and 32 in the outer conical side wall 14 of the guide means 12. The communications are by way of generally linear passageways 34 and 36 shown in phantom in FIGS. 2 and 3.

As can be seen, the passageways extend at divergent angles less than 90° from the longitudinal axis 16. Preferably, the angles are between 20° to 30° for one of the passageways and 25° to 35° for the other. More preferably, one of the passageways is at an angle of approximately 25° while the other is at an angle of approximately 30°. As is also known in the art, these passageways allow a surgical instrument carrying suture material to pass therethrough into the body to assist in closing the open wound.

Although the passageways 34 and 36 are shown as being of constant diameter, this is by way of example only. It is possible to make the upper part and/or the lower part of one or both of the passageways wider. This would allow the surgeon to manipulate the surgical instrument passing therethrough into different positions without having to move the entire device.

Extending upwardly from the top of the upper convex wall 24 at the proximal end 20 of the guide 12 is an elongated rod 38. Rod 38 is approximately 1.5 to 2.5 inches in length and most preferably about 2 inches. The diameter of the rod 38 is substantially less than the diameter of the guide means 12 but is axially aligned therewith. In the preferred embodiment of the invention, the diameter is approximately 3/16 of an inch. At the top of the rod 38 is a handle 40. As can be seen, the handle 40 is substantially cylindrical in shape but includes finger recesses 42 and 44 on opposite sides thereof in order to assist the surgeon in firmly grasping the same.

The handle 40 also includes an enlarged disk-shaped section 46 at the bottom thereof having a lower surface 48. The lower surface 48 is generally perpendicular to the longitudinal axis of the guide means 12 and is wider than the diameter of the proximal end 20 of the guide means. The purpose of this surface 48 is to prevent the device from entirely passing through the wound in the event that the same is lowered too far. The lower surface 48 would then simply rest on the outer surface of the patient's skin.

Preferably, the handle 40 is spaced from the proximal end 20 of the guide means 12 by a distance of between approximately 1.5 to 2.5 inches. More preferably, it is spaced approximately 2 inches from the guide means 12. This increases the visual field of the surgeon so that he or she can more accurately position the suturing device and avoid suturing the dermis. This also gives the surgeon the ability to tilt or turn or otherwise manipulate the position of the guide means 12 by maneuvering the handle 40 to aid in the suturing process.

The entire laparoscopic suturing guide device 10 can be machined in one piece from metal such as stainless steel or the like so that it can be sterilized and reused. It is not beyond the scope of the invention, however, to make the device from separate parts that are then connected together or to make the same from materials other than metal which may result in the device being disposable after one use.

The present invention may be embodied in other specific forms without departing from the spirit or essential attributes thereof and accordingly, reference should be made to the appended claims rather than to the foregoing specification as indicating the scope of the invention.

I claim:

1. A device for accurately guiding and positioning a surgical instrument bearing suture material to a predetermined area within the body for closing an open wound including:
    a guide means having a longitudinal axis and distal and proximal ends, said guide means being of substantially elongated conical shape with an outer conical wall having at least one opening therein and wherein said guide means is of smaller diameter at its distal end than at its proximal end, said distal end being adapted to be inserted into the wound;
    the proximal end of said guide means having a substantially convex upper wall with an opening therein;
    at least one generally linear passageway passing through said guide means between said opening in said conical wall and said opening in said upper wall and extending at a first diverging angle less than 90° from said longitudinal axis, said passageway allowing a surgical instrument carrying suture material to pass therethrough at said angle to the predetermined area within the body to assist in closing the open wound;
    an elongated rod extending upwardly from said upper wall, said rod being in substantial axial alignment with said guide means but having a diameter smaller than the diameter of the proximal end of said guide means, and
    a handle secured to the top of said rod and spaced from said guide means, a portion of said handle being substantially cylindrically shaped with finger recesses formed therein to assist in firmly grasping the same, said handle including a flange at the bottom thereof that is wider in diameter than said cylindrically shaped portion, said flange having a lower surface which is generally perpendicular to said longitudinal axis and which is wider than the diameter of said proximal end of said guide means to prevent said device from entirely passing through said wound.

2. The device as claimed in claim 1 further comprising a second opening in said conical wall, a second opening in said upper convex wall and a second passageway extending between said second openings and through said guide means forming a second angle less than 90° from said longitudinal axis.

3. The device as claimed in claim 2 wherein said second angle is between approximately 20° and approximately 30°.

4. The device as claimed in claim 1 wherein said handle is spaced from the proximal end of said guide means by a distance of between approximately 1.5 inches to approximately 2.5 inches.

5. The device as claimed in claim 1 wherein said first angle is between approximately 25° and approximately 35°.

6. A device for accurately guiding and positioning a surgical instrument bearing suture material to a predetermined area within the body for closing an open wound including:
- a guide means having a longitudinal axis and distal and proximal ends, said guide means being of substantially elongated conical shape with an outer conical wall having at least one opening therein and wherein said guide means is of smaller diameter at its distal end than at its proximal end, said distal end being adapted to be inserted into the wound;
- the proximal end of said guide means having a substantially convex upper wall with an opening therein;
- at least one generally linear passageway passing through said guide means between said opening in said conical wall and said opening in said upper wall, the entire length of said passageway extending at a first diverging angle less than 90° from said longitudinal axis, said passageway allowing a surgical instrument carrying suture material to pass therethrough at said angle to the predetermined area within the body to assist in closing the open wound;
- an elongated rod fixed to and extending upwardly from said upper wall, said rod being in substantial axial alignment with said guide means but having a diameter smaller than the diameter of the proximal end of said guide means, said rod being fixed to and immovable relative to said upper wall, and
- a handle secured to the top of said rod and spaced from said guide means, a portion of said handle being substantially cylindrically shaped with finger recesses formed therein to assist in firmly grasping the same, said handle including a flange at the bottom thereof that is wider in diameter than said cylindrically shaped portion, said flange having a lower surface which is generally perpendicular to said longitudinal axis and which is wider than the diameter of said proximal end of said guide means to prevent said device from entirely passing through said wound, said handle being fixed to and immovable relative to said rod.

7. The device as claimed in claim 6 further comprising a second opening in said conical wall, a second opening in said upper convex wall and a second passageway extending between said second openings and through said guide means, the entire length of said second passageway forming a second angle less than 90° from said longitudinal axis.

8. The device as claimed in claim 7 wherein said second angle is between approximately 20° and approximately 30°.

9. The device as claimed in claim 6 wherein said handle is spaced from the proximal end of said guide means by a distance of between approximately 1.5 inches to approximately 2.5 inches.

10. The device as claimed in claim 6 wherein said first angle is between approximately 25° and approximately 35°.

* * * * *